United States Patent
Egle et al.

(10) Patent No.: US 10,123,822 B2
(45) Date of Patent: Nov. 13, 2018

(54) MEDICAL INSTRUMENT, AND COUPLING MECHANISM FOR CONNECTING TWO STRUCTURAL PARTS OF A MEDICAL INSTRUMENT

(71) Applicant: Karl Storz SE & Co. KG, Tuttlingen (DE)

(72) Inventors: Michael Egle, Boettingen (DE); Rainer Hermle, Gosheim (DE); Claus Kramer, Immendingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 370 days.

(21) Appl. No.: 14/862,668

(22) Filed: Sep. 23, 2015

(65) Prior Publication Data

US 2016/0106463 A1 Apr. 21, 2016

(30) Foreign Application Priority Data

Sep. 23, 2014 (DE) .................. 10 2014 113 751

(51) Int. Cl.
*A61B 17/42* (2006.01)
*F16B 7/20* (2006.01)
*A61B 17/00* (2006.01)

(52) U.S. Cl.
CPC .......... *A61B 17/42* (2013.01); *A61B 17/4241* (2013.01); *F16B 7/20* (2013.01); *A61B 2017/00473* (2013.01); *A61B 2017/00477* (2013.01); *A61B 2017/4216* (2013.01)

(58) Field of Classification Search
CPC ................ A61B 17/42; A61B 17/4241; A61B 2017/00473
See application file for complete search history.

(56) References Cited

U.S. PATENT DOCUMENTS

| | | | | |
|---|---|---|---|---|
| 5,466,020 A | * | 11/1995 | Page | F16L 37/252 215/332 |
| 5,520,698 A | * | 5/1996 | Koh | A61B 17/4241 128/898 |
| 5,840,077 A | * | 11/1998 | Rowden | A61B 17/4241 606/119 |

(Continued)

FOREIGN PATENT DOCUMENTS

DE 19851268 C1 8/1999
DE 10257760 A1 6/2004

OTHER PUBLICATIONS

German Search Report Application No. DE 10 2014 113 751.5 Completed; Jul. 10, 2015; dated Jul. 16, 2015 10 pages.

(Continued)

Primary Examiner — Julie A Szpira
(74) Attorney, Agent, or Firm — Whitmyer IP Group LLC (57) ABSTRACT

A coupling mechanism for mechanically connecting a first structural part and a second structural part of a medical instrument includes a first component and a second component, which are designed to be connected to each other by a bayonet connection that permits a rotation of the second component relative to the first component about a rotation axis, and a detent mechanism for alternately locking the second component in several alternative and mutually different predetermined angle positions relative to the first component.

15 Claims, 4 Drawing Sheets

(56) References Cited

U.S. PATENT DOCUMENTS

| | | | |
|---|---|---|---|
| 2001/0021854 A1* | 9/2001 | Donnez | A61B 17/4241 606/119 |
| 2005/0085827 A1* | 4/2005 | G. | A61B 17/4241 606/119 |
| 2009/0131954 A1* | 5/2009 | Christian | A61B 17/4241 606/119 |
| 2011/0130769 A1* | 6/2011 | Boebel | A61B 17/4241 606/119 |
| 2012/0109146 A1* | 5/2012 | Auerbach | A61B 17/4241 606/119 |
| 2013/0066328 A1* | 3/2013 | Singh | A61B 17/42 606/119 |

OTHER PUBLICATIONS

European Search Report Application No. EP 15186390.9 Completed: Feb. 18, 2016; dated Feb. 25, 2016 9 pages.

* cited by examiner

MEDICAL INSTRUMENT, AND COUPLING MECHANISM FOR CONNECTING TWO STRUCTURAL PARTS OF A MEDICAL INSTRUMENT

FIELD OF THE INVENTION

The present invention relates to a medical instrument, in particular a uterine manipulator, and a mechanism for connecting two structural parts of such a medical instrument, the two structural parts of the medical instrument being movable relative to each other.

BACKGROUND OF THE INVENTION

Numerous medical instruments, in particular medical instruments for micro-invasive procedures, are able to be dismantled in order to permit complete cleaning of all the surfaces after each use. In some medical instruments, two or more structural parts are intended to be able to be moved relative to each other in the mechanically connected state. It is difficult, if not impossible, for both of these requirements to be met simultaneously, for example in uterine manipulators.

It is an object of the present invention to make available an improved coupling mechanism for mechanically connecting structural parts of a medical instrument, and to make available an improved medical instrument.

This object is achieved by the subject matter of the independent claims.

Developments are set forth in the dependent claims.

SUMMARY OF THE INVENTION

Illustrative embodiments of the present invention are based on the concept of forming a coupling mechanism composed of two components which can be connected to each other by a bayonet connection in such a way that they are connected to each other in several relative spatial configurations, in particular in several relative angle positions. In order to hold the two components releasably in each of several predetermined configurations, in particular angle positions, a detent mechanism in particular is provided.

A coupling mechanism of this kind can, for example in a first configuration, permit a fitting together and a non-destructive separation of structural parts of a medical instrument and, in a second configuration, can connect structural parts of the medical instrument to each other in such a way that they are movable relative to each other within a predetermined range but cannot be separated from each other, and, in a third configuration, can hold or lock structural parts of the medical instrument in a predetermined position or in one of several alternative predetermined positions or in any desired relative positions.

A coupling mechanism of this kind can in particular permit an especially simple design of a uterine manipulator in which the cap is removable from the shaft and, in the connected state, is movable along the shaft between two end positions and is optionally lockable in at least one position.

A coupling mechanism for mechanically connecting a first structural part and a second structural part of a medical instrument comprises a first component, a second component, wherein the first component and the second component are designed to be connected to each other by a bayonet connection that permits a rotation of the second component relative to the first component about a rotation axis in the connected state, and a detent mechanism for alternately locking the second component in a first predetermined angle position or in a second predetermined angle position relative to the first component.

The coupling mechanism is provided and designed in particular for mechanically connecting structural parts of a micro-invasive medical instrument, for example a tubular shaft instrument. Tubular shaft instrument designates any medical instrument that comprises a straight, curved or bendable, at least partially rigid or at least partially flexible shaft, wherein the shaft has in particular at least one rigid or flexible tube. Uterine manipulators and endoscopes, among others, are designated as tubular shaft instruments. The coupling mechanism can be designed for mechanically connecting structural parts, of which at least one is itself a medical instrument, in order to form a more complex medical instrument.

A bayonet connection is a connection that is produced by two components initially being moved toward each other in an in particular at least approximately linear movement and then being rotated relative to each other about an axis. The axis about which the second component in particular is rotated relative to the first component, in order to produce the mechanical connection of the two components, is in particular parallel to the direction of the preceding linear relative movement. The rotation axis of the rotation of the interconnected components relative to each other, as permitted by the bayonet connection, is in particular identical to or parallel to the axis about which the second component is rotated relative to the first component in order to form the bayonet connection.

The separability of the two components of the coupling mechanism at the bayonet connection is not to be confused with the separability of the structural parts of the medical instrument. Rather, the coupling mechanism, in one of its configurations or in a predetermined angle position of the second component relative to the first component, can permit a mechanical connection of structural parts of a medical instrument and, in another configuration or in another angle position of the second component relative to the first component connected thereto, can permit non-destructive separation of structural parts of the medical instrument. Thus, in both configurations of the coupling mechanism, the components thereof are connected to each other by the bayonet connection, including in the configuration in which the structural parts of the medical instrument can be separated non-destructively from each other.

The detent mechanism is in particular designed to releasably lock the second component alternately in one of several alternative and mutually different predetermined angle positions. Alternatively, the detent mechanism can be designed to lock the second component at least in one predetermined angle position relative to the first component such that it is non-releasable or such that it cannot be released without being destroyed.

The various predetermined configurations or angle positions of the second component relative to the first component, which are defined in particular by the detent mechanism alone, can correspond to several different actions of the coupling mechanism, which are effected by the various angle positions.

The coupling mechanism can in particular make cleaning easier and can permit the exchange or replacement of structural parts in the event of damage or defects or can permit adaptation to the specific requirements of a specific medical procedure on a specific patient. Moreover, by means of the bayonet connection between the components of the coupling mechanism, the coupling mechanism itself is easy to dismantle and can therefore be substantially or completely cleaned.

In the case of a coupling mechanism as described here, the coupling mechanism is provided and designed such that, in the first angle position, it permits a fitting together and a non-destructive separation of the first structural part and the second structural part of the medical instrument and, in the second angle position, it creates a mechanical connection of the first structural part and of the second structural part of the medical instrument.

In particular, the coupling mechanism is provided and designed such that, in the first angle position, it can be pushed together with the second component of the medical instrument onto a shaft as first structural part of the medical instrument. Thus, the coupling mechanism affords the possibility, for example, of pushing a cap or another work mechanism onto the shaft of a uterine manipulator, of connecting it thereto and of separating it again without destruction.

A coupling mechanism as described here is in particular provided and designed such that, in the second angle position, it connects the first structural part and the second structural part of the medical instrument in such a way that the second structural part is movable relative to the first structural part between a first predetermined end position and a second predetermined end position.

The coupling mechanism is in particular provided and designed such that, in the second angle position, it is movable, together with the work mechanism, linearly along a straight or curved shaft, for example, between a proximal end position and a distal end position.

In a coupling mechanism as described here, the detent mechanism is further provided and designed in particular to lock the second component relative to the first component alternatively in a third predetermined angle position, wherein the coupling mechanism is provided and designed such that, in the third angle position, it creates a substantially rigid connection of the first structural part and of the second structural part of the medical instrument.

Structural parts of a medical instrument are connected substantially rigidly if they can no longer be moved relative to each other, in particular if they can no longer be displaced relative to each other, setting aside unavoidable play, or play that cannot be avoided with reasonable effort, or play that is taken into account or desired in the sense of reasonable manufacturing costs or low friction.

In a coupling mechanism as described here, the detent mechanism in particular comprises one detent lug and several recesses which correspond to the detent lug and which predetermine the first angle position and the second angle position, or one recess and several detent lugs which correspond to the recess and which predetermine the first angle position and the second angle position.

The detent mechanism can have several detent lugs and several recesses or depressions in order to lock the second component relative to the first component in all angle positions in which at least one detent lug engages in an opposite and corresponding recess. The one or more detent lugs are each themselves elastic in particular or are arranged on an elastic mechanism so as to be able to be deflected counter to an elastic force and moved out of the recess.

In particular, the one or more recesses are provided on the first component (for example rigidly or elastically connected to the first component) and the one or more detent lugs are provided on the second component (for example rigidly or elastically connected to the second component). Alternatively or in addition, one or more detent lugs are provided on the first component and one or more recesses are provided on the second component.

In a coupling mechanism as described here, at least either a detent lug or a recess of the detent mechanism is in particular elastically deflectable in a direction that is substantially parallel to the rotation axis. A direction is substantially parallel to the rotation axis about which the second component is rotatable relative to the first component when the direction and the rotation axis enclose an angle of not more than 45 degrees or not more than 30 degrees or not more than 20 degrees or not more than 10 degrees or not more than 5 degrees.

In a coupling mechanism as described here, at least either a detent lug or a recess of the detent mechanism is elastically deflectable in a direction that is substantially orthogonal to the rotation axis.

A direction is substantially orthogonal to the rotation axis about which the second component is rotatable relative to the first component when the angle between the direction and the rotation axis is in the range of 45 degrees to 90 degrees or in the range of 60 degrees to 90 degrees or in the range of 70 degrees to 90 degrees or in the range of 80 degrees to 90 degrees or in the range of 85 degrees to 90 degrees.

In a coupling mechanism as described here, a detent lug of the detent mechanism is arranged in particular on a strip-shaped, elastic mechanism secured at one end or at both ends.

The detent lug is in particular arranged at the free end of a strip-shaped, elastic mechanism secured or fixed at one end. Alternatively, the detent lug can be arranged between the ends, in particular centrally between the ends of a strip-shaped elastic mechanism secured or fixed at both ends. Alternatively, several detent lugs of the detent mechanism or one or more recesses can be arranged on the strip-shaped, elastic mechanism. The strip-shaped, elastic mechanism in particular forms a miniaturized elastic bar that is fixed at one end or at both ends. The strip-shaped, elastic mechanism can be formed by an L-shaped incision (in particular for securing at one end) or by a straight cut (particularly in the case of securing at both ends) on an edge of the first component or of the second component.

In a coupling mechanism as described here, the elastic mechanism is in particular formed integrally with the first component or integrally with the second component.

In a coupling mechanism as described here, the first component and the second component are in particular each substantially tubular, wherein the first component is arranged at least partially in the second component when the second component is connected to the first component by the bayonet connection.

In a coupling mechanism as described here, the first component and the second component are in particular each substantially tubular, wherein the second component is arranged at least partially in the first component when the second component is connected to the first component by the bayonet connection.

The first component and the second component are thus in particular arranged coaxially when they are mechanically connected by the bayonet connection. In particular, the first component and the second component each have at least in part the shape of the jacket surface of a circular cylinder or of a straight truncated cone with a circular base surface.

A coupling mechanism as described here in particular encloses a substantially cylindrical interior, wherein the second component has an area protruding into the cylindrical interior, at least in one angle position.

A coupling mechanism as described here in particular encloses a substantially circular cylindrical interior, wherein the first component has an area protruding into the circular cylindrical interior, and the second component has an area protruding into the circular cylindrical interior.

The coupling mechanism is provided in particular for coupling to a circular cylindrical shaft that has one or more grooves or flat surfaces. The coupling mechanism can then, for example, be moved parallel to the longitudinal axis of the shaft when both inwardly protruding areas on the two components engage in the same or two different grooves or flat surfaces. At places on the shaft where the latter has a groove extending in the circumferential direction, the second component can for example be rotated relative to the first component while the inwardly protruding area of the second component engages in the circumferentially extending groove. This can permit a locking of the coupling mechanism at the location of the circumferentially extending groove or can carry the inwardly protruding area on the second component into another groove or flat surface parallel to the longitudinal axis of the shaft.

In a coupling mechanism as described here, the first component has in particular a collar, wherein the detent mechanism is arranged on the collar on the first component and on an edge of the second component lying opposite the collar.

In particular, the one or more recesses of the detent mechanism are arranged on the collar on the first component and the one or more detent lugs are arranged on the edge of the second component lying opposite the collar on the first component. Alternatively or in addition, one or more detent lugs of the detent mechanism can be arranged on the collar on the first component, and one or more recesses of the detent mechanism can be arranged on the edge of the second component lying opposite the collar on the first component.

In particular, the one or more recesses open in the axial direction, and the one or more detent lugs engage in the axial direction in the one or more recesses. The extent by which the collar protrudes from the first component corresponds in particular to the wall thickness of the second component plus the play between the inner wall of the second component and the outer wall of the first component.

If the first component is arranged substantially inside the second component, the collar can protrude outward. If the second component is arranged substantially inside the first component, a collar with corresponding features and properties can protrude inward. In both cases, as an alternative to or in addition to a collar on the first component, a collar protruding in the opposite direction and having corresponding features can be provided on the second component.

A medical instrument comprises a first structural part, a second structural part, and a coupling mechanism, as described here, for mechanically connecting the first structural part and the second structural part of the medical instrument.

One of the two components of the coupling mechanism, in particular the first component of the coupling mechanism, can be connected rigidly and non-releasably to one of the two structural parts of the medical instrument, in particular produced integrally with this structural part or, after separate production, can be joined thereto by cohesive bonding or by force-fit and/or form-fit engagement.

A medical instrument comprises a shaft, a work mechanism for working on part of a human or animal body, and a coupling mechanism with several predetermined configurations, for mechanically connecting the work mechanism to the shaft, wherein a first configuration of the coupling mechanism permits a fitting together and a non-destructive separation of work mechanism and shaft, and wherein, in a second configuration of the coupling mechanism, the work mechanism is mechanically connected to the shaft in such a way that the work mechanism is movable along the shaft between a proximal position and a distal position.

The shaft has in particular one or more grooves or flat surfaces, which extend in the longitudinal direction of the shaft, and one or more grooves extending in the circumferential direction, wherein the coupling mechanism has the described inwardly protruding areas on the first component and on the second component, which areas engage in the grooves and/or flat surfaces.

A medical instrument as described here is in particular provided and designed for micro-invasive medical procedures. A medical instrument as described here is in particular a medical tubular shaft instrument, for example a uterine manipulator.

The work mechanism is provided in particular for working mechanically and/or electrosurgically on an organ or tissue of a human or animal body, for example for retaining, resecting or obliterating. The work mechanism comprises, for example, a cap of a uterine manipulator.

In a medical instrument as described here, particularly in a third configuration of the coupling mechanism, the work mechanism is locked in a position on the shaft.

In the third configuration of the coupling mechanism, the work mechanism is locked in particular in a predetermined position or in one of several predetermined positions on the shaft. The locking is effected, for example, by the inwardly protruding area on the first component engaging in a groove or recess that extends in the longitudinal direction of the shaft and by the inwardly protruding area of the second component engaging in a groove that extends in the circumferential direction on the shaft, or vice versa.

In a medical instrument as described here, the coupling mechanism in particular comprises a first component, which is connected to the work mechanism, and a second component, which is rotatable relative to the first component about the longitudinal axis of the shaft and which, in various configurations of the coupling mechanism, adopts different angle positions relative to the first component.

In a medical instrument as described here, the coupling mechanism is in particular a coupling mechanism as described here.

In a medical instrument as described here, the coupling mechanism comprises in particular a collet chuck or another mechanism for force-fit connection of the first structural part to the second structural part of the instrument.

The collet chuck is in particular designed such that, by axial displacement and/or rotation of one component relative to another component, it moves one or more wedges, jaws or other at least also radially movable mechanisms radially inward, in order to form a force-fit connection or frictional connection.

A medical instrument as described here is in particular a uterine manipulator.

BRIEF DESCRIPTION OF THE DRAWINGS

Embodiments are explained in more detail below with reference to the attached figures, in which.

DETAILED DESCRIPTION OF THE INVENTION

Figure 1:
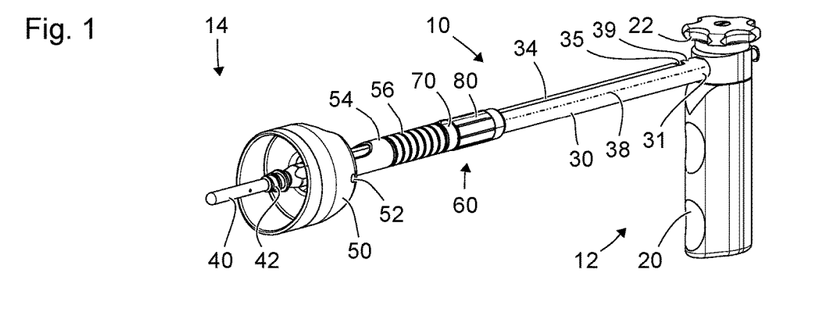
FIG. 1 shows a schematic axonometric view of a uterine manipulator.

FIG. 1 shows a schematic view of a uterine manipulator 10 with a proximal end 12 and a distal end 14. A rotatable handle 20 with a rotary wheel 22 for locking purposes is provided at the proximal end 12 of the uterine manipulator 10. The uterine manipulator 10 comprises a shaft 30 with a proximal end 31, which is connected to the handle 20, with a joint (not visible in FIG. 1) and with a distal end (likewise not visible in FIG. 1) near the distal end 14 of the uterine manipulator 10. The shaft 30 has substantially the shape of a circular cylinder.

In a departure from the ideal shape of a circular cylinder, the shaft 30 has a first flat surface 34, extending in the longitudinal direction of the shaft 30, a first groove 35 extending in the circumferential direction of the shaft 30 and arranged near the proximal end 31, and further flat surfaces and grooves not visible in FIG. 1. The flat surface 34 extends straight and parallel to the longitudinal axis 38 of the shaft 30. In the area of the flat surface 34, the outer contour of the cross section of the shaft 30 is not curved in the shape of an arc of a circle but instead straight. A recess 39 is moreover provided at the proximal end 31 of the shaft 30.

A working insert 40 with a thread 42 for form-fit connection to the uterus is provided at the distal end of the shaft 30. The working insert 40 is in particular connected releasably to the distal end of the shaft 30, for example by a screw connection or bayonet connection. The working insert 40 is in particular exchangeable for other working inserts with the same or different features, dimensions and other properties. This not only simplifies cleaning and sterilization, it also allows the uterine manipulator 10 to be used with different working inserts for different medical procedures.

The uterine manipulator 10 further comprises a cap 50 made of ceramic or of another material and connected to a tube 54 via a joint 52. The tube 54 has an inner cross section which matches the outer cross section of the shaft 30, such that the tube 54 together with the cap 50 is movable, with low play and friction, along the shaft 30 parallel to the longitudinal axis 38 thereof. On the outer surface of the tube 54, a ribbing 56 is provided in the form of circumferential grooves in order to permit a secure hold of the tube 54. In the illustrated distal position of the cap 50 and of the tube 54, the pivot axes of the joint (not visible in FIG. 1) near the distal end 33 of the shaft 30 coincide with the pivot axes of the joint 52 between 50 and tube 54.

At the proximal end of the tube 56, a coupling mechanism 60 with a first component 70 and a second component 80 is provided. The second component 80 is movable, for example rotatable, relative to the first component 70 between different positions, in particular between different positions that are predetermined by detents. The first component 70 of the coupling mechanism 60 is connected rigidly to the tube 54, for example joined by cohesive bonding or by a force fit and/or form fit, or is originally produced in one piece therewith.

The various predetermined positions of the second component 80 relative to the first component 70 of the coupling mechanism 60 represent different configurations of the coupling mechanism 60 that have different functions. In particular in a first configuration of the coupling mechanism 60, the cap 50 together with the tube 54 and with the coupling mechanism 60 can be pushed, from the direction of the distal end, over the shaft 30 of the uterine manipulator 10 (if appropriate over the working insert 40 already connected to the distal end of the shaft 30). In a second configuration of the coupling mechanism 60, for example, the tube 54 together with the coupling mechanism 60 and the cap 50 can be moved relative to the shaft 30 between the distal end position shown in FIG. 1 and a proximal end position, but without being able to be completely separated again from the shaft 30. In a third configuration of the coupling mechanism 60, for example, the tube 54 together with the cap 50 and the coupling mechanism 60 can be locked in a predetermined position or in one of several predetermined positions or in any desired position between the predetermined end positions.

The handle 20 is rotatable about a rotation axis orthogonal to the longitudinal axis 38 of the shaft 30 and parallel to the plane of the drawing in FIG. 1. The rotation axis of the handle 20 is in particular at the same time the rotation axis of the rotary wheel 22 for locking the handle 20. The handle 20 is coupled to the distal end 33 of the shaft, by one or more mechanisms in the interior of the shaft 30, in such a way that a rotation of the handle 20 is associated with a pivoting movement of the distal end of the shaft 30, and of the working insert 40 rigidly connected to the distal end, about the pivot axis of the joint (not visible in FIG. 1) near the distal end of the shaft 30.

The cap 50 and/or the joint 52 between the cap 50 and the tube 54 are designed such that the cap 50, in its distal position shown in FIG. 1, is coupled to the distal end of the shaft 30 with a form fit. A pivoting movement of the distal end of the shaft 30 and of the working insert 40, effected by rotation of the handle 20, is therefore associated with a corresponding pivoting movement of the cap 50. Therefore, in the distal position of the tube 54 and of the coupling mechanism 60 as shown in FIG. 1, the cap 50 has a predetermined position relative to the distal end 33 of the shaft 30 and relative to the working insert 40, independently of the angle position of the distal end of the shaft 30 adjustable by the handle 20.

Figure 2:
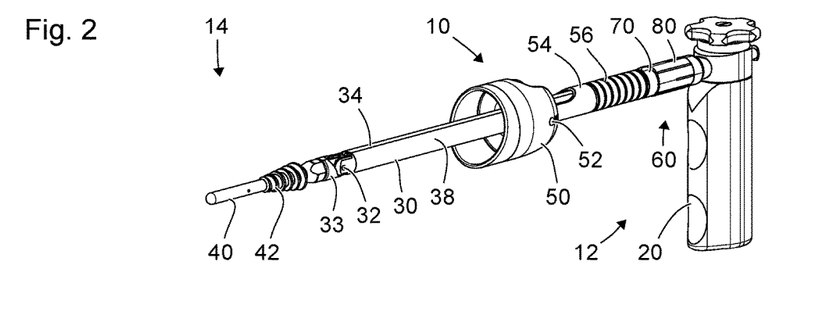
FIG. 2 shows a further schematic axonometric view of the uterine manipulator from FIG. 1.

FIG. 2 shows a further schematic axonometric view of the uterine manipulator from FIG. 1. The nature of the view corresponds to that of FIG. 1.

In FIG. 2, the unit composed of cap 50, tube 54 and coupling mechanism 60 is shown in a proximal end position, or in an extreme proximal position, relative to the shaft 30. In FIG. 2, the distal end 33 of the shaft 30 and the joint 32 near the distal end 33 of the shaft 30 are visible.

Figure 3:
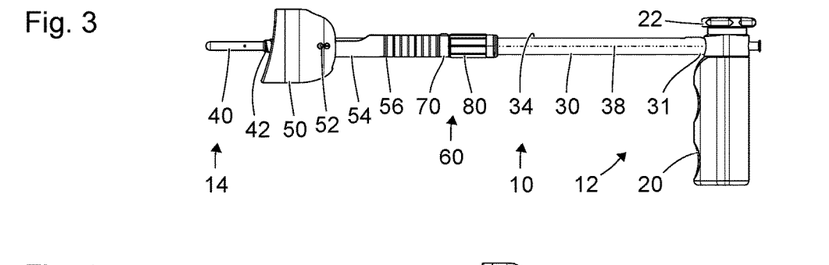
FIG. 3 shows a further schematic view of the uterine manipulator from FIGS. 1 and 2.

FIG. 3 shows a further schematic view of the uterine manipulator from FIGS. 1 and 2. In contrast to FIGS. 1 and 2, FIG. 3 shows a side view rather than an axonometric view. The plane of the drawing in FIG. 3 is parallel to the longitudinal axis 38 of the shaft 30 and to the rotation axis of the handle 20.

The unit composed of cap 50, tube 54 and coupling mechanism 60 is located in the distal position also shown in FIG. 1. The pivot axis of the joint 32 near the distal end 33 of the shaft 30 (cf. FIG. 2) coincides in this situation with that of the joint 52 between cap 50 and tube 54 and is orthogonal to the plane of the drawing in FIG. 3.

Figure 4:
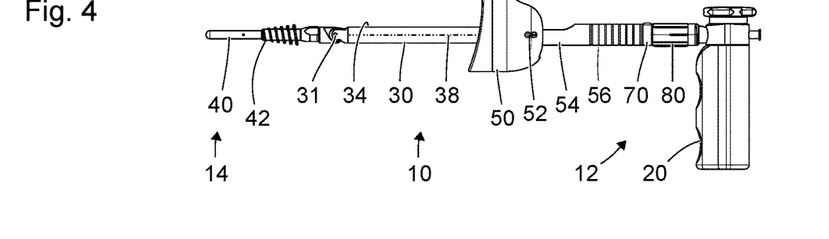
FIG. 4 shows a further schematic view of the uterine manipulator from FIGS. 1 to 3.

FIG. 4 shows a further schematic view of the uterine manipulator 10 from FIGS. 1 to 3. The nature of the view corresponds to that of FIG. 3.

In the situation shown in FIG. 4, the unit composed of cap 50, tube 54 and coupling mechanism 60 is located in the proximal end position shown in FIG. 2.

Figure 5:
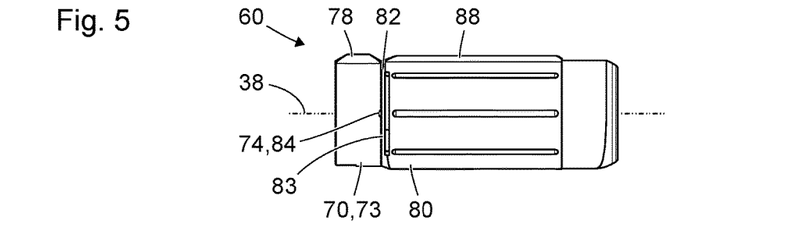
FIG. 5 shows a schematic view of a coupling mechanism of the uterine manipulator from FIGS. 1 to 4.

FIG. 5 shows a schematic view of an embodiment of the coupling mechanism 60 of the uterine manipulator shown in FIGS. 1 to 4. The coupling mechanism 60 is shown enlarged by comparison with FIGS. 1 to 4. Otherwise, the nature of the view corresponds to that of FIGS. 3 and 4.

In the coupling mechanism 60 shown in FIG. 5, the second component 80 is rotatable relative to the first component 70 about a rotation axis which, when the uterine manipulator is fitted together, corresponds to the longitudinal axis 38 of the shaft 30 (cf. FIGS. 1 to 4). The various configurations of the coupling mechanism 60 correspond to different angle positions of the second component 80 relative to the first component 70 of the coupling mechanism 60.

Figure 6:
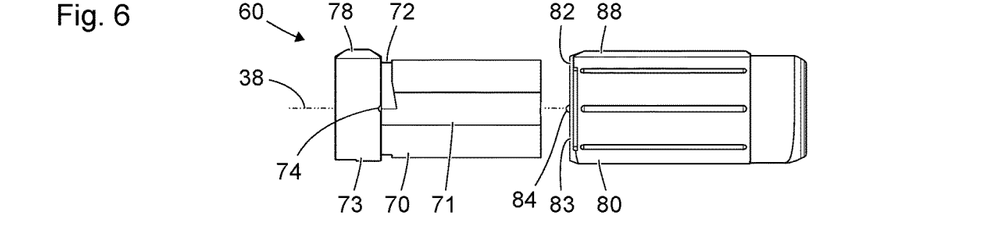
FIG. 6 shows a further schematic view of the coupling mechanism from FIG. 5.

FIG. 6 shows a further schematic view of the coupling mechanism from FIG. 5. The nature of the view corresponds to that of FIG. 5.

In FIG. 6, the first component 70 and the second component 80 of the coupling mechanism 60 are shown separated from each other. The first component 70 and also the second component 80 are both substantially tubular or have substantially the shape of jacket surfaces of circular cylinders. The first component 70 for the most part has an external diameter slightly smaller than the internal diameter of the second component 80, so as to allow the first component 70 to be guided with minimal play and friction in the second component 80.

In a departure from an ideally circular cylindrical shape, the first component 70 has a flat surface 71 extending in the longitudinal direction of the first component 70, and a groove 72 extending in the circumferential direction of the first component 70. The flat surface 71 in particular extends straight and parallel to the rotation axis 38. In the area of the flat surface 71 of the first component 70, the outer contour of the cross section of the first component 70 is not in the shape of an arc of a circle but instead straight. The groove 72 does not encircle the first component 70 completely, but instead by three quarters in the example shown. The depth of the groove 72 corresponds to the depth of the flat surface 71.

Moreover, in a departure from an ideally circular cylindrical shape, the first component 70 has a radially outwardly protruding collar 73 on its distal edge facing toward the tube 54 (cf. FIGS. 1 to 4). A recess 74 is provided on the proximal edge of the collar 73 facing toward the second component 80. Moreover, the collar 73 has a marking 78 in the form of an axially extending web.

On its distal edge 82 facing toward the collar 73 of the first component 70, the second component 80 has an elastic, strip-shaped area 83 with a first detent lug 84 protruding distally in the axial direction. The elastic, strip-shaped area 83 is separated from the rest of the second component in particular by a straight cut or a narrow window, such that both ends of the elastic, strip-shaped area are connected rigidly to the rest of the second component 80. The first detent lug 84 is arranged in the middle of the elastic, strip-shaped area 83. The shape of the first detent lug 84 corresponds to the shape of the recess 74 on the collar 73 of the first component 70.

Moreover, the second component 80 has a marking 88 in the form of an axially extending web.

It can be seen from FIG. 5 how the first detent lug 84 on the elastic, strip-shaped area 83 engages in the recess 74 on the collar 73 of the first component 70 and thus, by form-fit engagement, defines a predetermined angle position of the second component 80 relative to the first component 70. Several recesses 74, in particular three recesses 74, are provided on the collar 73 of the first component 70, said recesses being arranged at angular intervals of 90 degrees. Thus, three predetermined angle positions of the second component 80 relative to the first component 70 are defined by form-fit engagement.

Figure 7:
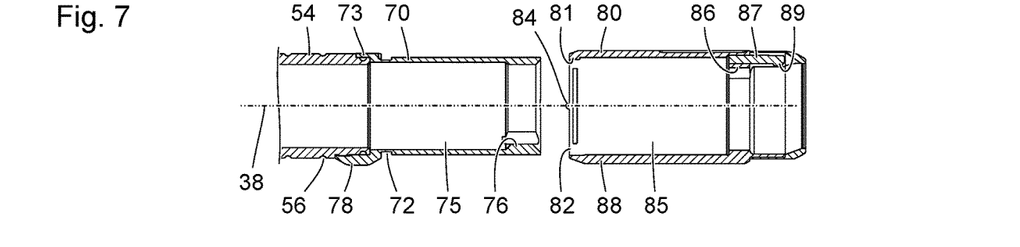
FIG. 7 shows a schematic view of a longitudinal section through the coupling mechanism from FIGS. 5 and 6.

FIG. 7 shows a schematic view of a section through the coupling mechanism 60 from FIGS. 5 and 6. The section plane of FIG. 7 is parallel to the drawing planes of FIGS. 5 and 6 and contains the rotation axis or longitudinal axis 38 of the shaft 30 that is to be inserted into the coupling mechanism 60. However, the viewing direction of the section plane as shown in FIG. 7 is counter to the viewing direction shown in FIGS. 5 and 6, in order to make visible the elastic, strip-shaped area 83 on the second component 80. In accordance with the inverted viewing direction, the marking 78 on the first component 70 and the marking 88 on the second component 80 are arranged at the bottom in the view in FIG. 7.

The view in FIG. 7 further differs from the views in FIGS. 5 and 6 in that the proximal end of the tube 54 is shown with a ribbing 56. The proximal end of the tube 54 is joined to the distal edge of the first component 70 in particular by welding, soldering, adhesive bonding or by some other form of cohesive bonding, or by force-fit and/or form-fit engagement. The proximal edge of the tube 54 and the distal edge of the first component 70 overlap in order to improve the robustness of the connection of the tube 54 and of the first component 70 of the coupling mechanism 60.

The first component 70 encloses a substantially circular cylindrical interior 75, into which an inwardly protruding area 76 of the first component 70 protrudes. The function of the inwardly protruding area 76 of the first component 70 is explained with reference to FIGS. 9 to 11.

The second component 80 encloses a substantially circular cylindrical interior 85, of which the cross section corresponds substantially to the outer cross section of the first component 75 in the area located proximally from the collar 73. The second component 80 has an inwardly protruding area 81. In the longitudinal section shown in FIG. 7, the area 81 has a shape corresponding to the groove 72 on the first component 70. In cross section, or in the section along a plane orthogonal to the longitudinal axis 38 of a shaft 30 to be inserted into the coupling mechanism 60 (cf. FIGS. 1 to 4), the area 81 has a shape corresponding to the flat surface 71 on the first component 70.

The area 81 of the second component 80 protruding into the interior 85 of the second component 80, on the one hand, and the flat surface 71 (cf. FIG. 6) and the groove 72 on the first component 70, on the other hand, form a bayonet connection for form-fit engagement and releasable mechanical connection of the components 70, 80 of the coupling mechanism 60. When the second component 80 is suitably oriented with respect to the first component 70, the second component 80 can be fitted onto the first component 70 or pushed over the latter by means of a straight translational movement. During this straight translational movement, the area 81 protruding into the interior 85 of the second component 80 engages in the flat surface 71 on the first component 70. By means of a subsequent rotational movement of the second component 80 relative to the first component 70, the area 81 of the second component 80 protruding into the interior 85 can be inserted into the groove 72 on the first component 70, and the second component 80 can be brought into one of the angle positions defined by the first detent lug 84 and the recesses 74, in which positions the components 70, 80 of the coupling mechanism 60 are mechanically connected to each other.

The second component 80 moreover has an area 86, which protrudes into the interior 85 of the second component 80. The area 86 protrudes farther into the interior 85 than does the area 81.

The second component 80 moreover has a pin 87, which extends in a direction parallel to the rotation axis 38 and which, at its distal end, is connected mechanically rigidly to the inwardly protruding area 86 of the second component 86. A second detent lug 89 is provided at the free end of the pin 87. The pin 87 can be elastic.

The second detent lug 89 on the second component 80 can latch into the recess 39 (cf. FIG. 1) so as to make it possible to feel or hear when the proximal end position shown in FIGS. 2 and 4 is reached, and so as to hold the coupling mechanism 60, and with it the tube 54 and the cap 50, releasably in this end position. Corresponding further recesses (not visible in FIG. 1) can be provided at other locations on the shaft 30 so as to make it possible to feel or hear when corresponding positions are reached, and so as to hold the coupling mechanism 60, with the tube 54 and the cap 50, in these positions.

Figure 8:
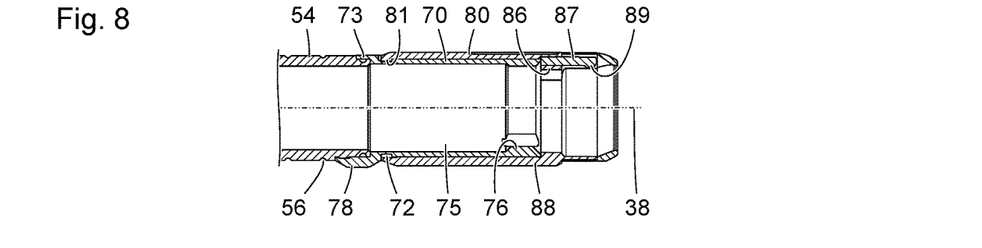
FIG. 8 shows a further schematic view of a longitudinal section through the coupling mechanism from FIGS. 5 to 7.

FIG. 8 shows a further schematic view of a section through the coupling mechanism 60 from FIGS. 5 to 7. The nature of the view in FIG. 8, in particular the section plane, corresponds to that of FIG. 7. However, in contrast to the situations shown in FIGS. 6 and 7, the components 70 and 80 of the coupling mechanism 60 are not shown separate from each other. Instead, FIG. 8 shows the situation shown in FIG. 5, in which the components 70, 80 of the coupling mechanism 60 are connected to each other.

The area 81 on the second component 80 engages in the groove 72 on the first component and thus holds the components 70, 80 together by form-fit engagement. The inwardly protruding area 76 on the first component 70, the inwardly protruding area 86 on the second component 80, and the second detent lug 89 on the second component 80 protrude into the circular cylindrical space defined by the interior of the tube 54 and by the interior 75 of the second component 70. The function of the inwardly protruding areas 76, 86 on the components 70, 80 is described with reference to FIGS. 9 to 11.

Figure 9:
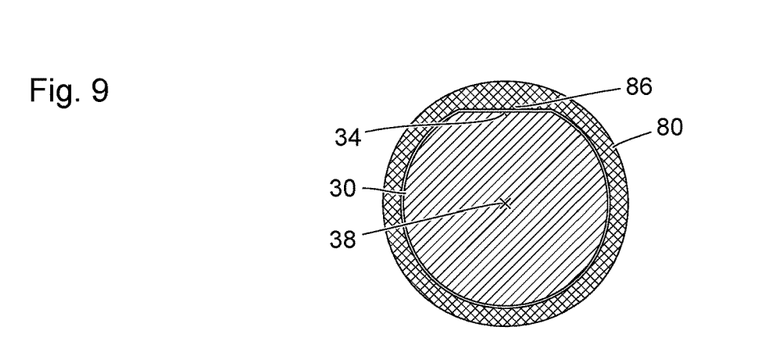
FIG. 9 shows a schematic view of a cross section through the shaft of the uterine manipulator from FIGS. 1 to 4, with the coupling mechanism from FIGS. 5 to 8.

FIG. 9 shows a schematic view of a section through the uterine manipulator as shown in FIGS. 1 to 4, with the coupling mechanism as shown in FIGS. 5 to 9. In FIG. 9, a section through the uterine manipulator is shown in a situation in which the unit composed of cap 50, tube 54 and coupling mechanism 60 is arranged farther in the distal direction relative to the shaft 30 than is shown in FIGS. 1 and 3. The section plane of FIG. 9 lies close to the proximal edge of the second component 80 and intersects the inwardly protruding area 86 thereof. FIG. 9 does not show the interior of the shaft 30, which in particular accommodates mechanisms for coupling a rotational movement of the handle 20 to a pivoting movement of the distal end 33 of the shaft 30, of the working insert 40 and of the cap 50 (cf. FIGS. 1 to 4).

The shaft 30 has the described first flat surface 34, which extends in a direction parallel to the longitudinal axis 38 of the shaft 30 and in the area of which the outer contour of the shaft 30 is not shaped as an arc of a circle but is instead straight. The shape of the inwardly protruding area 86 on the second component 80 corresponds to the flat surface 34 on the shaft 30. In this way, the angle position of the second component 80 relative to the shaft 30 is fixed.

Figure 10:
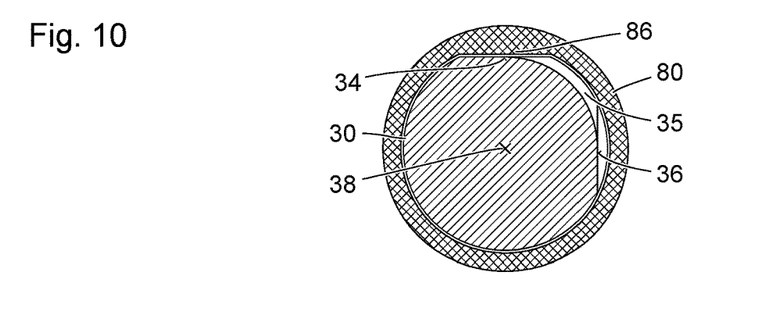
FIG. 10 shows a further schematic view of a cross section through the shaft of the uterine manipulator from FIGS. 1 to 4, with the coupling mechanism from FIGS. 5 to 8.

FIG. 10 shows a schematic view of a section through the uterine manipulator 10 as shown in FIGS. 1 to 4, with the coupling mechanism 60 as shown in FIGS. 5 to 8. The nature of the view corresponds to that of FIG. 9. In FIG. 10, a section through the uterine manipulator is shown in the situation as shown in FIGS. 2 and 4 in which the unit composed of cap 50, tube 54 and coupling mechanism 60 is located in the proximal end position relative to the shaft 30. The section plane of FIG. 10 lies close to the proximal edge of the second component 80, intersects the inwardly protruding area 86 thereof and lies in the first groove 35 on the shaft 30, which groove 35 extends in the circumferential direction of the shaft 30.

In a direction parallel to the circumference of the shaft 30, the groove 35 connects the first flat surface 34 to a second flat surface 36, which extends parallel to the first flat surface 34 and to the longitudinal axis 38 of the shaft 30. The inwardly protruding area 86 on the second component 80 and the first groove 35 are adapted to each other in such a way that the inwardly protruding area 86 can be moved in the first groove 35. Therefore, proceeding from the angle position shown in FIG. 10, the second component 80 can be rotated clockwise through approximately 90 degrees.

Figure 11:
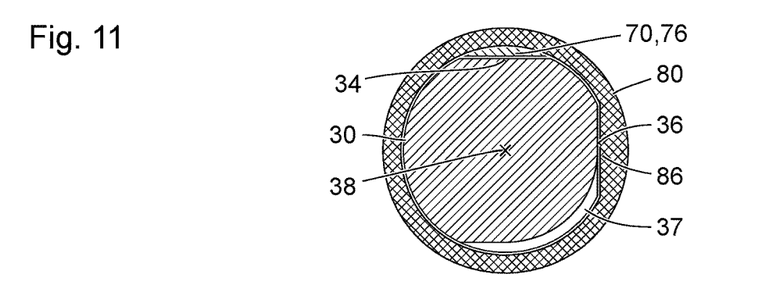
FIG. 11 shows a further schematic view of a cross section through the shaft of the uterine manipulator from FIGS. 1 to 4, with the coupling mechanism from FIGS. 5 to 8.

FIG. 11 shows a schematic view of a section through the uterine manipulator 10 as shown in FIGS. 1 to 4, with the coupling mechanism 60 as shown in FIGS. 5 to 8. The nature of the view corresponds to that of FIGS. 9 and 10. In FIG. 11, a section through the uterine manipulator is shown in the situation as shown in FIGS. 1 and 3 in which the unit composed of cap 50, tube 54 and coupling mechanism 60 is located in the distal end position relative to the shaft 30. The section plane of FIG. 10 lies close to the proximal edge of the second component 80, intersects the inwardly protruding area 86 thereof and lies in a second groove 37 on the shaft 30, which groove 37 extends in the circumferential direction of the shaft 30.

Proceeding from the second flat surface 36, the groove 37 extends in a direction away from the first flat surface 34 by an angle of approximately 90 degrees. The inwardly protruding area 86 on the second component 80 and the second groove 37 are adapted to each other in such a way that the inwardly protruding area 86 can be moved in the second groove 37. Therefore, proceeding from the position shown in FIG. 11, the second component 80 can be rotated clockwise through an angle of approximately 90 degrees.

The inwardly protruding area 76 of the first component 70 is visible in FIG. 11, which area 76 engages in the first flat surface 34 on the shaft 30. The form-fit engagement between the inwardly protruding area 76 of the first component 70 and the flat surface 34 on the shaft 30 has the effect that the first component 70, and with it the tube 54 and the cap 50 (cf. FIGS. 1 to 4), cannot be rotated about the longitudinal axis 38 of the shaft 30.

Figure 12:
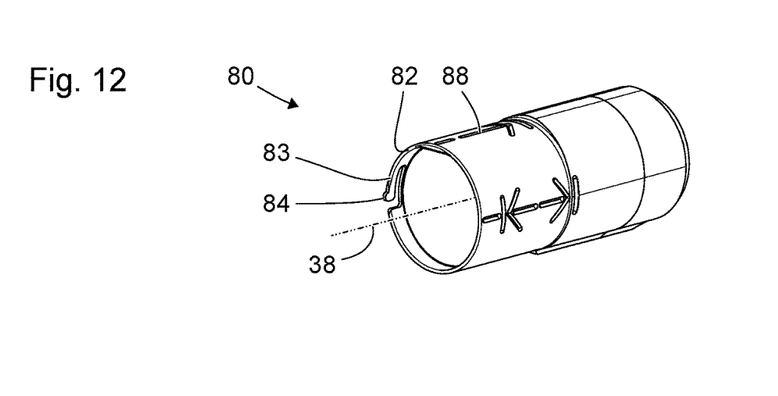
FIG. 12 shows a schematic axonometric view of an alternative embodiment of part of a coupling mechanism.

FIG. 12 shows a schematic axonometric view of a second component 80 of a further embodiment of a coupling mechanism 60 of the uterine manipulator 10 shown in FIGS. 1 to 4. In terms of some features, properties and functions, the second component 80 shown in FIG. 8 is similar to the second component of the coupling mechanism shown in FIGS. 5 to 11. The second component 80 shown in FIG. 12 is in particular provided to be combined with the first component 70 shown in FIGS. 5 to 11, or with a similar component, in order to form a coupling mechanism. Features, properties and functions are in particular described below in which the second component 80 shown in FIG. 12 differs from the second component shown in FIGS. 5 to 11.

The second component 80 shown in FIG. 12 differs from the second component of FIGS. 5 to 11 particularly in terms of the fact that the first detent lug 84 is arranged at the free end of an elastic, strip-shaped area 83 which is fixed only at one end or is rigidly connected only at the opposite end to the rest of the second component 80. In contrast to the embodiment shown in FIGS. 5 to 11, the elastic, strip-shaped area 83 is not formed by a straight section but instead by an L-shaped section at the distal edge 82 facing toward the collar 73 of the first component 70 (cf. FIGS. 5 to 8).

In the coupling mechanism shown in FIG. 12, markings 88 for the predetermined angle positions are not provided in the form of a web, but instead in the form of symbols that are engraved (laser-printed) into the outer surface of the second component 80.

Figure 13:
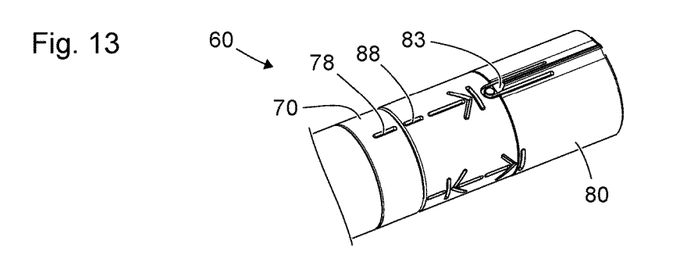
FIG. 13 shows a schematic axonometric view of a further alternative embodiment of a coupling mechanism.

FIG. 13 shows a schematic axonometric view of a further embodiment of a coupling mechanism of the uterine manipulator 10 shown in FIGS. 1 to 4, which coupling mechanism, in terms of some features, properties and functions, is similar to the coupling mechanisms shown in FIGS. 5 to 12. Features, properties and functions are in particular described below in which the coupling mechanism 60 shown in FIG. 13 differs from the coupling mechanisms shown in FIGS. 5 to 12.

In the coupling mechanism shown in FIG. 13, the elastic, strip-shaped area 83 is not arranged at the distal edge of the second component 80 and is not parallel to the circumference; instead it is oriented parallel to the longitudinal axis. One end of the elastic, strip-shaped area 83 is connected rigidly to the rest of the second component 80. At the other, opposite end, a detent lug (not visible in FIG. 13) is provided which engages radially inward in a recess (likewise not visible in FIG. 13) in the first component 70. In contrast to the embodiments shown in FIGS. 5 to 12, the elastic, strip-shaped area 83 is not formed by a straight or L-shaped section but instead by a U-shaped section.

Figure 14:
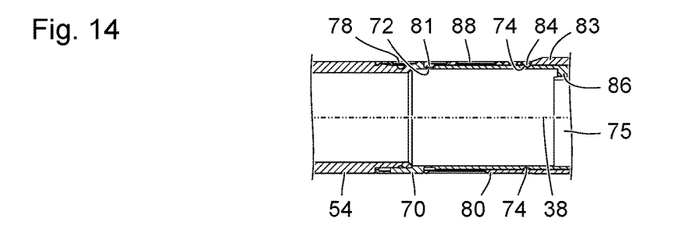
FIG. 14 shows a schematic view of a longitudinal section through the coupling mechanism from FIG. 13.

FIG. 14 shows a schematic view of a section through the coupling mechanism 60 as shown in FIG. 13. The section plane contains the longitudinal axis 38 of a shaft 30 to be inserted into the coupling mechanism 60 (cf. FIGS. 1 to 4 and 9 to 11), about which longitudinal axis 38 the second component 80 is rotatable relative to the first component 70.

In the situation shown in FIG. 14, the first detent lug 84 at the free end of the elastic, strip-shaped area 83 engages in one of several corresponding recesses 74 on the outer surface of the first component 70. If the second component 80 is rotated out from the predetermined position shown in FIGS. 13 and 14, the first detent lug 84 is deflected counter to the elastic force of the elastic, strip-shaped area 83 not, as in the embodiments shown in FIGS. 5 to 12, in an axial direction or in a direction parallel to the rotation axis 38, but instead in a radial direction or a direction orthogonal to the rotation axis 38.

Figure 15:
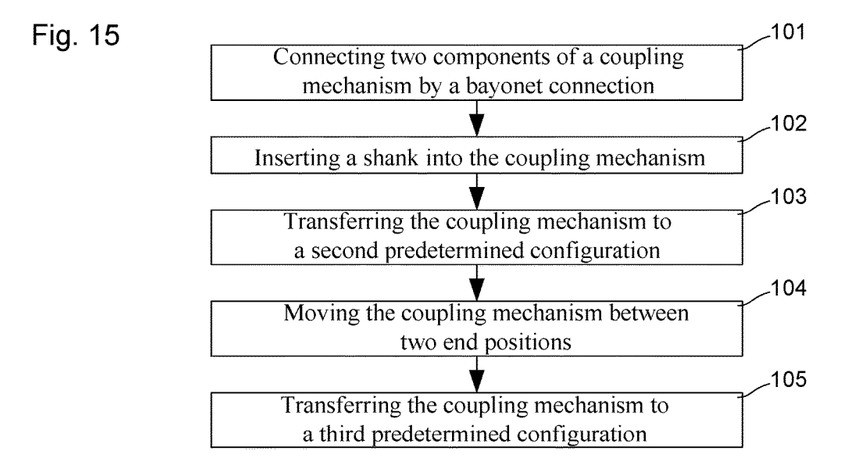
FIG. 15 shows a schematic flow chart of a method for preparing for use of a medical instrument.

FIG. 15 shows a schematic flow chart of a method for preparing a uterine manipulator or another medical instrument for use in a medical procedure. Although the method can also be carried out with medical instruments that have features, properties and functions deviating from those shown in FIGS. 1 to 14, reference signs from FIGS. 1 to 14 are used below in order to make matters clearer.

In an optional first step 101, two components 70, 80 of a coupling mechanism 60 are connected to each other by a bayonet connection. The first step 101 is in particular carried out after a preceding use and a subsequent cleaning of the coupling mechanism. The coupling mechanism is in particular at all times, or at the time of execution of the first step 101, part of a structural part 50, 54, 60 of a medical instrument 10, in particular of a uterine manipulator. In particular, the first component 70 of the coupling mechanism 60 is permanently and rigidly connected to the structural part 50, 54 or to a part 54 thereof. In particular, a first configuration of the coupling mechanism 60 is produced in which the second component 80 adopts a first predetermined angle position relative to the first component 70 of the coupling mechanism 60.

In a second step 102, a shaft 30, as part of a second structural part 20, 30, 40 of the medical instrument 10, is inserted into the coupling mechanism 60 in its first predetermined configuration. The coupling mechanism 60, in its first predetermined configuration, is in particular pushed over the shaft 30 from the direction of the distal end 33.

In a third step 103, the coupling mechanism 60 is transferred to a second configuration in order to connect the coupling mechanism 60 to the shaft 30. For this purpose, the second component 80 of the coupling mechanism is in particular brought into a second predetermined angle position, corresponding to the second predetermined configuration, relative to the first component 70 of the coupling mechanism 60. In this way, the coupling mechanism 60 is in particular mechanically connected to the shaft 30 in such a way that the coupling mechanism 60 moves relative to the shaft and, therefore, the structural part 20, 30, 40 and the structural part 50, 54, 60 of the medical instrument 10 move relative to each other within a predetermined range but can no longer be separated from each other.

In an optional fourth step 104, the coupling mechanism 60 can be moved to and fro between two end positions, in particular along a straight linear path. In this way, the structural part 20, 30, 40 and the structural part 50, 54, 60 of the medical instrument 10 can also be moved relative to each other between the predetermined end positions.

In an optional fifth step 105, the coupling mechanism 60 is transferred to a third predetermined configuration, in particular by rotating the second component 80 to a third predetermined angle position of the second component 80 relative to the first component 70 of the coupling mechanism 60, corresponding to the third predetermined configuration. In the third predetermined configuration, the coupling mechanism 60 is locked on the shaft 30 in a predetermined position or in one of several predetermined positions or in any desired position between the two end positions.

The invention claimed is:

1. A coupling mechanism for mechanically connecting a first structural part and a second structural part of a medical instrument, comprising:
   a first component;
   a second component, wherein the first component and the second component are designed to be connected to each other by a bayonet connection that permits a rotation of the second component relative to the first component about a rotation axis in the connected state;
   a detent mechanism for alternately locking the second component in a first predetermined angle position or in a second predetermined angle position relative to the first component;
   wherein the detent mechanism comprises one detent lug and several recesses which correspond to the detent lug and which predetermine the first predetermined angle position and the second predetermined angle position, or one recess and several detent lugs which correspond to the recess and which predetermine the several different angle positions; and
   wherein either at least one of the detent lugs of the detent mechanism or at least one of the recesses of the detent mechanism is elastically deflectable in a direction that is substantially parallel to the rotation axis.

2. The coupling mechanism according to claim 1, wherein the coupling mechanism is provided and designed such that, in the first angle position, the coupling mechanism permits a fitting together and a non-destructive separation of the first structural part and the second structural part of the medical instrument and, in the second angle position, the coupling mechanism creates a mechanical connection of the first structural part and of the second structural part of the medical instrument.

3. The coupling mechanism according to claim 1, wherein the coupling mechanism is provided and designed such that, in the second angle position, the coupling mechanism connects the first structural part and the second structural part of the medical instrument in such a way that the second structural part is movable relative to the first structural part between a first predetermined end position and a second predetermined end position.

4. The coupling mechanism according to claim 2, wherein the detent mechanism is further provided and designed to lock the second component relative to the first component alternatively in a third predetermined angle position; and
   wherein the coupling mechanism is provided and designed such that, in the third angle position, it creates a substantially rigid connection of the first structural part and of the second structural part of the medical instrument.

5. The coupling mechanism according to claim 3, wherein the detent mechanism is further provided and designed to lock the second component relative to the first component alternatively in a third predetermined angle position; and
   wherein the coupling mechanism is provided and designed such that, in the third angle position, the coupling mechanism creates a substantially rigid connection of the first structural part and of the second structural part of the medical instrument.

6. The coupling mechanism according to claim 1, wherein either at least one of the detent lugs or at least one of the recesses of the detent mechanism is elastically deflectable in a direction that is substantially orthogonal to the rotation axis.

7. The coupling mechanism according to claim 6, wherein at least one of the detent lugs of the detent mechanism is arranged on a strip-shaped, elastic mechanism secured at one end or at both ends.

8. The coupling mechanism according to claim 1, wherein at least one of the detent lugs of the detent mechanism is arranged on a strip-shaped, elastic mechanism secured at one end or at both ends.

9. The coupling mechanism according to claim 1, wherein the first component and the second component are each substantially tubular, and in which the first component is arranged at least partially in the second component when the second component is connected to the first component by the bayonet connection.

10. The coupling mechanism according to claim 1, wherein the coupling mechanism encloses a substantially circular cylindrical interior;
    wherein the first component has an area protruding into the circular cylindrical interior; and
    wherein the second component has an area protruding into the circular cylindrical interior.

11. The coupling mechanism according to claim 1, wherein the first component has a collar, and
    the detent mechanism is arranged on the collar and on an edge of the second component lying opposite the collar.

12. A medical instrument, comprising:
    a shaft;
    a work mechanism for working on part of a human or animal body;
    a coupling mechanism with several predetermined configurations, for mechanically connecting the work mechanism to the shaft;
    wherein a first configuration of the coupling mechanism permits a fitting together and a non-destructive separation of the work mechanism and the shaft,
    wherein, in a second configuration of the coupling mechanism, the work mechanism is mechanically connected to the shaft in such a way that the work mechanism is movable along the shaft between a proximal position and a distal position;
    wherein the coupling mechanism comprises:
       a first component;
       a second component, wherein the first component and the second component are designed to be connected to each other by a bayonet connection that permits a rotation of the second component relative to the first component about a rotation axis in the connected state; and
       a detent mechanism for alternately locking the second component in a first predetermined angle position or in a second predetermined angle position relative to the first component, wherein the detent mechanism comprises one detent lug and several recesses which correspond to the detent lug and which predetermine the first predetermined angle position and the second predetermined angle position, or one recess and several detent lugs which correspond to the recess and which predetermine the several different angle positions; and
       wherein either at least one of the detent lugs of the detent mechanism or at least one of the recesses of the detent mechanism is elastically deflectable in a direction that is substantially parallel to the rotation axis.

13. The medical instrument according to claim 12, wherein in a third configuration of the coupling mechanism, the work mechanism is locked in a position on the shaft.

14. The medical instrument according to claim 12, wherein the first component of the coupling mechanism is connected to the work mechanism, and
the second component, is rotatable relative to the first component about the longitudinal axis of the shaft and, in various configurations of the coupling mechanism, adopts different angle positions relative to the first component.

15. The medical instrument according to claim 13, wherein the first component of the coupling mechanism is connected to the work mechanism, and the second component is rotatable relative to the first component about the longitudinal axis of the shaft and, in various configurations of the coupling mechanism, adopts different angle positions relative to the first component.

* * * * *